United States Patent
Rugenstein

(10) Patent No.: US 6,695,804 B2
(45) Date of Patent: Feb. 24, 2004

(54) DEVICE FOR REMOVAL OF FATTY DEBRIS FROM BLOOD

(76) Inventor: Charles Dennis Rugenstein, 9129 Kinlock Dr., Indianapolis, IN (US) 46256-2239

( * ) Notice: Subject to any disclaimer, the term of this patent is extended or adjusted under 35 U.S.C. 154(b) by 15 days.

(21) Appl. No.: 09/841,575

(22) Filed: Apr. 24, 2001

(65) Prior Publication Data

US 2002/0156412 A1 Oct. 24, 2002

(51) Int. Cl.$^7$ .................. A61M 37/00; B01D 11/00; B01D 61/00
(52) U.S. Cl. ............ 604/5.03; 604/4.01; 210/645; 210/646; 210/650
(58) Field of Search .............. 604/4.01, 5.03, 604/6.13, 6.14; 210/645, 668, 782, 348, 511, 646, 647, 650, 252, 257, 321.6, 321.72, 32.79; 422/44, 48, 45

(56) References Cited

U.S. PATENT DOCUMENTS

| | | | |
|---|---|---|---|
| 4,775,482 A | * 10/1988 | Thurman | .................. 210/668 |
| 5,242,644 A | * 9/1993 | Thompson et al. | .... 264/177.15 |
| 5,423,738 A | * 6/1995 | Robinson et al. | .......... 604/6.01 |
| 5,785,685 A | 7/1998 | Kugler et al. | |
| 5,792,157 A | 8/1998 | Mische et al. | |
| 5,836,868 A | 11/1998 | Ressemann et al. | |
| 5,843,022 A | 12/1998 | Willard et al. | |
| 5,879,624 A | * 3/1999 | Boehringer et al. | ........ 210/645 |
| 5,897,567 A | 4/1999 | Ressemann et al. | |
| 5,904,146 A | 5/1999 | Plaia et al. | |
| 5,904,698 A | 5/1999 | Thomas et al. | |
| 5,916,227 A | 6/1999 | Keirh et al. | |
| 5,934,284 A | 8/1999 | Plaia et al. | |
| 5,938,670 A | 8/1999 | Keith et al. | |
| 5,941,895 A | 8/1999 | Myler et al. | |
| 5,957,929 A | 9/1999 | Brenneman | |
| 5,968,070 A | 10/1999 | Bley et al. | |
| 5,972,019 A | 10/1999 | Engelson et al. | |
| 6,321,915 B1 | * 11/2001 | Wilson et al. | .............. 210/505 |
| 6,350,411 B1 | * 2/2002 | Cho et al. | ............ 261/DIG. 28 |

OTHER PUBLICATIONS

U.S. patent application Ser. No. 09/483,406, Rugenstein, Filed Jan. 14, 2000.

* cited by examiner

Primary Examiner—William C. Doerrler
Assistant Examiner—Filip Zec
(74) Attorney, Agent, or Firm—Mark A. Manley

(57) ABSTRACT

This invention is a device for removing occlusive fatty plaque from vascular blood of humans. The action of fatty plaque removal occurs by pumping vascular blood through the device.

The device consists of a super-absorbent melt-blown microfiber oleophilic material, structural support for this absorbent material and an outer containment vessel in which the cleansing of blood is performed. Patient blood is directed from the circulatory system to a catheter and then to a pump and the device. After having been cleansed of fatty plaque, blood is directed back through a second catheter to the patient's circulatory system.

15 Claims, 4 Drawing Sheets

DEVICE FOR REMOVAL OF FATTY DEBRIS FROM BLOOD

FIELD OF THE INVENTION

This invention concerns a device that comprises oleophilic absorption media for absorbing fatty plaque suspended in blood, support for the oleophilic absorption media and an outer vessel for containing vascular blood, oleophilic absorption media and said media support structure. The device of this invention is used in combination with a pump for pumping of blood and three catheters that connect the device, the pump and the patient blood vessel.

BACKGROUND OF THE INVENTION

Vascular occlusions restrict or reduce the flow of blood throughout blood vessels. There are several existing devices and surgical techniques presently in use to loosen and extricate vascular occlusions, and restore or increase blood flow. Unfortunately, these devices and techniques have unpredictable, and therefore undesirable, side effects due to their inability to securely remove substantially all of the offending occlusive material from the patient.

Some procedures, such as angioplasty, create room for increased blood flow through or around an occlusion by compressing the occlusive plaque material against the inner walls of the occluded blood vessel. Portions of the occlusive plaque material often resist this compression. They can then flow freely through the affected blood vessel to other areas of the circulatory system. This free flow of plaque can lead to a secondary occlusive buildup in the patient, causing a heart attack, brain hemorrhage, stroke, or even death.

This invention incorporates the use of a device for removal of fatty debris suspended in vascular blood. This device is capable of completely removing suspended, loose occlusive plaque material from the patient. Complete removal of the occlusive plaque will minimize the undesirable collateral effects of loosened material causing further blockages in blood vessels.

The use of this device is similar to dialysis procedure for renal patients. As external dialysis removes excess urinary waste, this device removes suspended, undesirable fatty vascular occlusive material. Processing of blood through renal dialysis machinery serves to eliminate unwanted urinary material. This device similarly removes suspended, unwanted loose fatty debris (vascular plaque) from blood.

This device for removal of fatty debris present in vascular blood also presents the advantage of eliminating the need for secondary vascular surgery in many patients. Secondary vascular surgery may be required to correct occluded blood flow resulting from primary occlusion removal surgery.

DISTINCTIVE FEATURES

Several existing devices are available for the mitigation of vascular occlusions, but only this device provides for the complete removal of suspended fatty vascular debris resulting from all forms of vascular surgery. The surgical removal of vascular plaque simultaneously with vascular blood cleansing by use of occlusive fatty plaque oleophilic absorption media is advantageous, since subsequent occlusions caused by loosened plaque will therefore be much less likely to occur.

It is also highly desirable to remove the surgically loosened plaque so that secondary vessel blockage does not result. All of this can be done simultaneous with or following vascular surgery.

SUMMARY OF THE PRESENT INVENTION

The present invention significantly advances the art of surgical removal of fatty occlusions and obstructions within the cardiovascular or peripheral vascular systems of humans and animals. It does so by separately or by simultaneously cleansing the blood of surgery patients. The process of blood cleansing occurs external to the patient.

The device comprises two chambers with a membrane between them. The membrane comprises super-absorbent oleophilic material and a porous support structure. The two chambers and the membrane are located within an outer containment vessel.

Use of the device is made by removing patient blood through a catheter, pumping it through the device, conducting the cleansed blood through a return catheter and back into the patient's circulatory system.

Removal of fatty vascular debris occurs by presenting vascular blood to this device which contains super-absorbent oleophilic microfibers. This super-absorbent oleophilic material selectively attracts and holds loose fatty debris. The elimination of fatty vascular debris from the patient is affected by discarding the super-absorbent material after use.

Angioplasty, one of the medical treatments currently in use, presses fatty offending material against the inside wall of an occluded blood vessel. This action can cause pieces of the occlusion to break loose and subsequently circulate in the patient's vascular system. Such treatment may result in additional vascular occlusions elsewhere in the body, or even death.

Surgical implantation of stents will similarly cause portions of fatty vascular plaque to break loose and circulate through the patient after surgery. The surgical procedure for which the present invention is intended provides a more effective removal of the occlusive material from a blood vessel than could result from a common surgical procedure alone. This is accomplished by the cleansing of vascular blood during or after vascular surgery by fat-absorbing oleophilic material.

DETAILED DESCRIPTION OF FIGURES

The device is made up of several parts. An outer vessel contains the operative components of this invention as well as inlet and outlet chambers and connection ports to the patient. Inside the outer containment vessel is placed the super-absorbent oleophilic material. A porous supportive structure is placed to support the super-absorbent oleophilic material. This supportive structure may be separate from or integral with the outer vessel. A structure such as porous disks may be used as the supportive structure.

Outer vessel material is of any nature that can be formed in fabrication processes. The material of construction may be polymer, fiber or metal. The outer containment vessel construction material must be unaffected by the aqueous nature of blood. The functions of containment of the patient blood and of the constituent parts of the device are all that are necessary. Construction materials and design are not otherwise critical choices to the performance of this device. Example construction design is not limited to that shown. As long as the critical functions of blood containment and structural support are provided, the device will perform satisfactorily.

Materials used for the outer containment vessel, porous support structure and oleophilic super-absorbent polymeric microfibers must not attract and hold the normally desired blood components. As with urinary dialysis, materials must be chosen which will not remove normal, desired blood components.

Since the bulk properties of the super-absorbent oleophilic material are such that it is easily deformable, the oleophilic super-absorbent material must be effectively held within the outer vessel without collapsing the open structure of the oleophilic material.

Super-absorbent oleophilic material is held so that it is presented to the flow of blood through the device. As blood flows through the device, the fatty occlusive material suspended within the blood is attracted to and held by the individual fibers of the super-absorbent oleophilic material. The oleophilic material is not a clarifying filter. The space between individual oleophilic material fibers must be large enough to allow desired blood components to pass through the super-absorbent oleophilic material fibers. The action of the super absorbent oleophilic material fibers is to selectively attract and retain the undesirable fatty particles suspended in the blood, not to retain the fatty particles or any other blood components by physical obstruction.

Structural support for the super-absorbent oleophilic material is provided by a porous structure which is not subject to aqueous effects such as swelling, softening and corrosion. The structural support is accomplished by material that allows the super-absorbent oleophilic material to be constrained from movement through the device as blood flows through the device.

FIGURE 1

Figure 1:
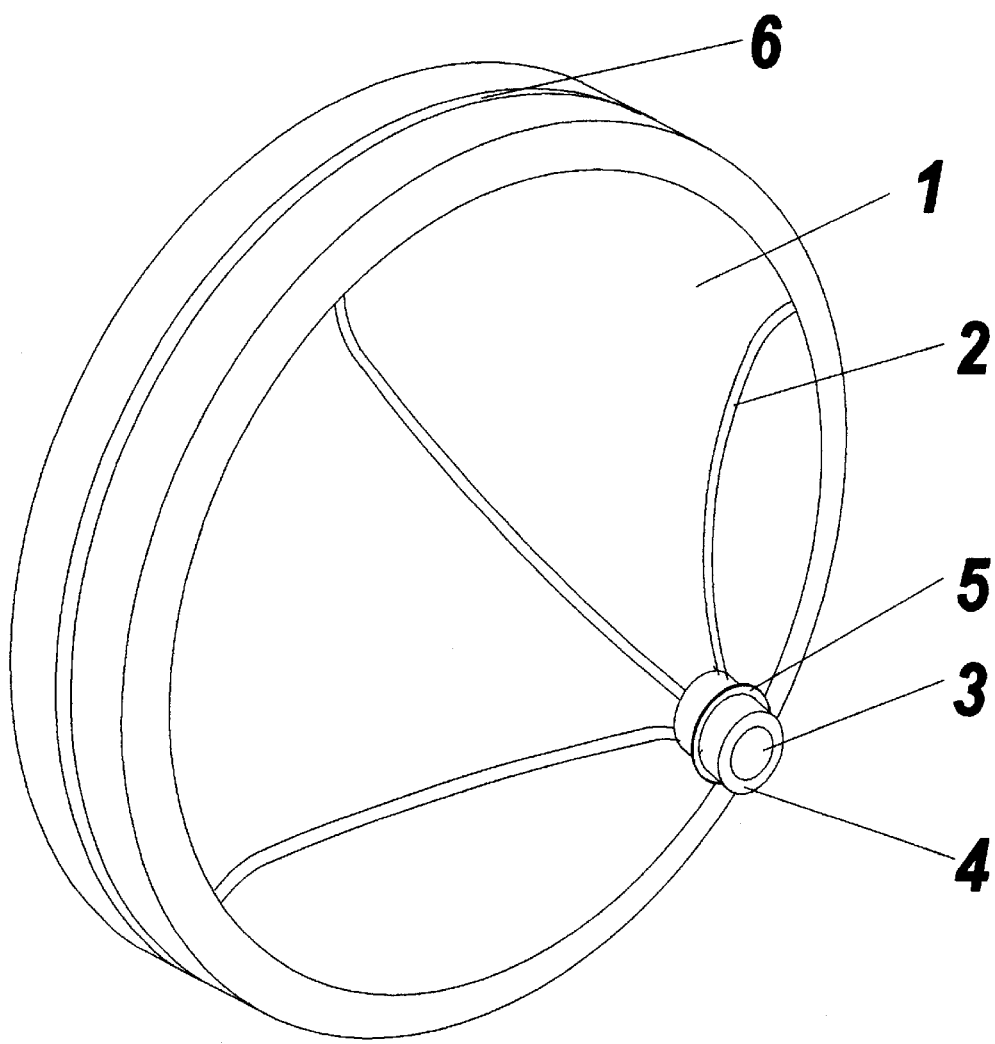
FIG. 1 is a perspective view of the outer surfaces of the device with details of the inlet port of the assembly shown.

FIG. 1 is a perspective view of the outer surfaces of the outer containment vessel of the device with details of the right end of the assembly shown.

The outer vessel 1 provides for sterile blood processing and containment. Vascular blood is forced into the device through inlet port 3. A catheter conveying patient blood is connected to the inlet port 3. This tubing is held in place by being slipped over the inlet port connector 4 and held securely by the barb ridge 5. Stiffening ribs 2 are desirable but not essential for rigidity of the outer containment vessel. Left and right shell halves comprising the outer containment vessel are welded together with the fusion bead 6. Internal parts of the device are not shown in FIG. 1.

The view of this figure is primarily that of the inlet port shell half. The outlet port shell half is very similar to that of the inlet port shell shown.

FIGURE 2

Figure 2:
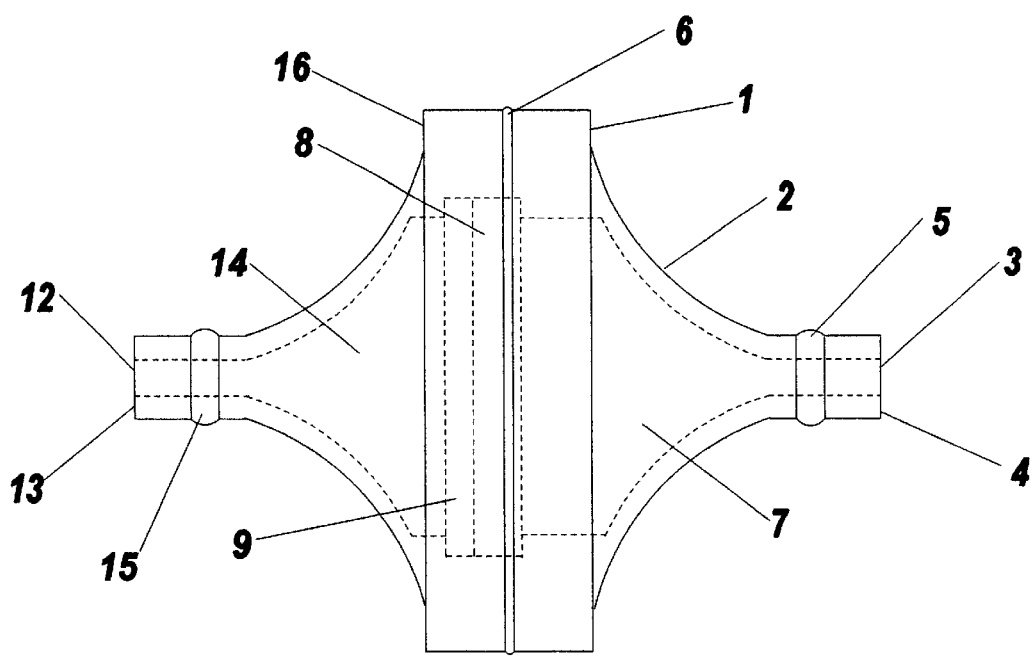
FIG. 2 is a side view of the device. It shows the outer surfaces of the device with the inner components as hidden line features.
Figure 3:
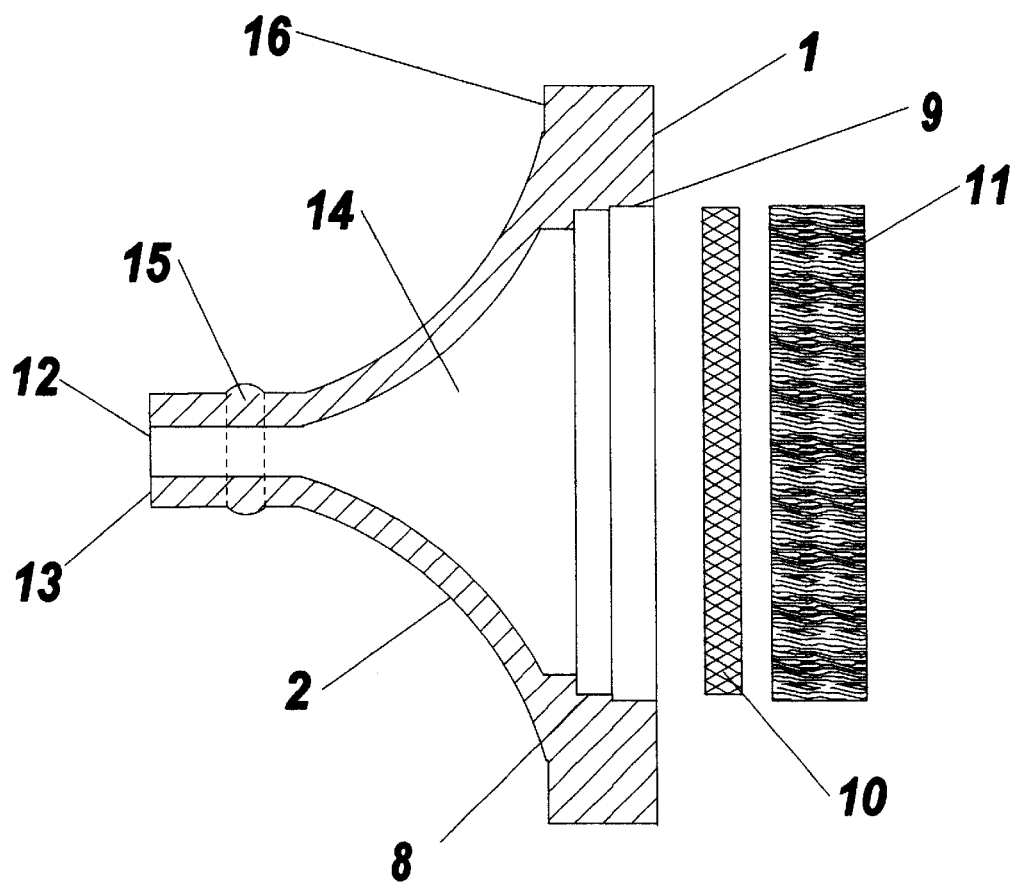
FIG. 3 is an exploded view of the outlet port and shell of the device of FIG. 2 but with the super-absorbent oleophilic material and the porous support structure shown separated from the outer enclosure.

FIG. 2 shows the entire device in a side view. The internal elements of the device are shown as hidden lines. As with FIG. 1, the blood enters the device through the inlet port 3. A catheter conveys patient blood to the inlet port 3 and is held in place by the inlet port connector 4 and the barb ridge 5. Patient blood, after entering the device through the inlet port 3, enters the internal (inlet) chamber 7. Pumped, pressurized blood inside the inlet chamber 7 is forced into contact with and subsequently through the super-absorbent oleophilic material held in cavity 8. The super-absorbent oleophilic material is held in place by the porous support structure contained in cavity 9. The porous support structure 10, not shown in this view but rather in FIG. 3, is held in place within the cavity 9 in the outer containment vessel. A second internal (outlet) chamber 14 is downstream of the porous support structure cavity 9. The blood, which has passed through the super-absorbent oleophilic material 11, not shown in this view but rather in FIG. 3, enters the second internal (outlet) chamber 14. From the internal (outlet) chamber 14, blood is forced to exit the device through the outlet port 12. A second catheter, which conveys patient blood from the outlet port 12 back to the patient, is connected to the outlet port connector 13. This outlet port catheter returns cleansed blood to the patient.

FIGURE 3

FIG. 3 is an exploded view of the outlet portion of the containment vessel, absorbent material and its support structure.

Pumped, pressurized blood inside the inlet chamber 7 of FIG. 2 is forced into contact with and subsequently through the super-absorbent oleophilic material 11. Blood is caused to flow from the right (inlet) chamber of FIG. 2, through the super-absorbent oleophilic material 11, through the porous support structure 10 and then into the outlet chamber 14. The super-absorbent oleophilic material 11 is held in place by the porous support structure 10 and cavity 8. The porous support structure 10 is held within cavity 9 of the outer vessel 16 in which it resides. A catheter conveys cleansed patient blood from the outlet chamber 14, through the outlet port 12 and back to the patient. The outlet catheter is attached to the outlet port connector 13 and the barb ridge 15 at one end and to the blood vessel of the patient at the other end. The absorbent material 11 is a polyolefin microfiber. The porous support structure 10 is present so that it can hold the absorbent material 11 in place. It also supports the absorbent material 11 so that the transiting blood is free to flow through the absorbent material 11 without the absorbent material 11 moving away from its cavity 8.

FIGURE 4

Figure 4:
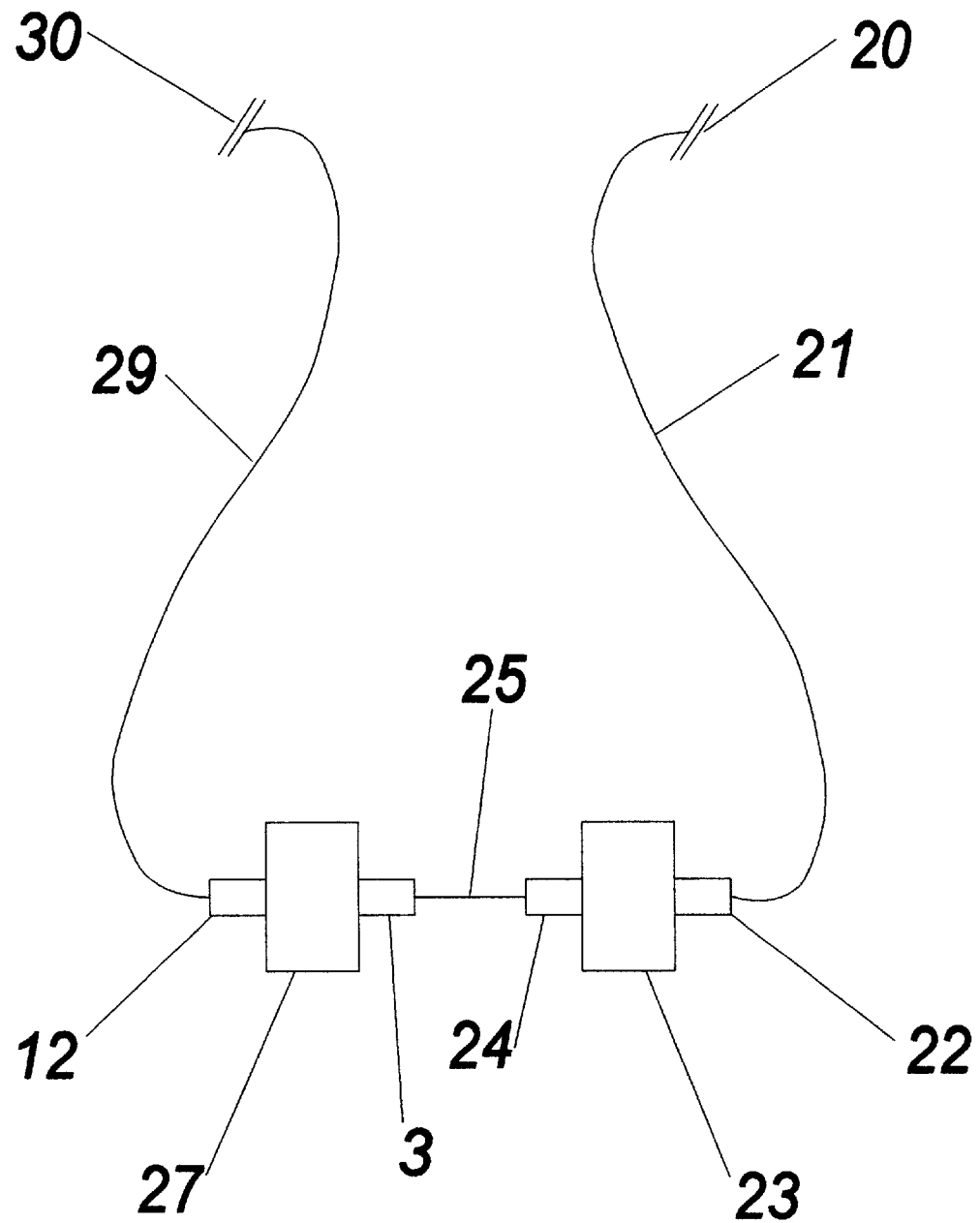
FIG. 4 is a schematic of the device with the device and a pump connected to a patient blood vessel, prepared for surgical cleansing of patient blood.

FIG. 4 is a schematic view of the device of this application 27 with the associated devices necessary for successful use by a surgeon.

Connection point 20 is the connection between inlet catheter 21 and the patient blood vessel located downstream of the vascular obstruction. The other end of catheter 21 is connected to blood pump inlet 22. A blood pump 23 is required for the pumping of patient blood through the device of this application 27. Pump outlet 24 supplies pressurized blood from pump 23 to the device of this application 27. A tube 25 passes pressurized blood from the outlet of the pump 24 to the inlet of this device 3. Blood is cleansed by passage through this device 27. Cleansed blood passes through the outlet of this device 12 and into the return catheter 29. Cleansed blood is returned to the patient through return catheter 29, through the connection point 30 and into the patient blood vessel.

DETAILED DESCRIPTION

The purpose of surgical removal of occlusive plaque and fatty blood components from within the vascular system of an individual is to provide a larger passage for the critical vascular fluids within and to potentially eliminate the further deposit of occlusive plaque. One common cause for these obstructions is the deposit of undesired materials upon the inner walls of such blood vessels. These obstructions may be composed of either oleophilic or oleophobic type materials. Oleophilic or oleophobic materials are those that are attracting or repelling of fatty substances respectively.

In the detailed description of the device which is the subject of this application for patent, the term "this device" and "the device" are used to refer to the device and its construction as detailed herein.

An example of vascular obstructive oleophilic type material is fatty plaque related to elevated blood cholesterol. Another example is fibrin, which may be attached to the vascular wall itself, or to the plaque which is attached to the vascular wall. Fatty plaque is frequently mobile enough to be easily displaced, translated and transported by externally applied force, while fibrin is generally not mobile enough for such action to move it.

Removal of vascular fatty plaque is beneficial because a surgeon may thus increase inner vascular area. The device of this application is useful in removing undesirable fatty plaque from the vascular system of a patient during or after vascular surgery. The movement of blood out from a blood vessel and through this device removes offending fatty debris.

As blood flows through this device, porous disks provide a means by which mobile fatty material may be allowed to come into direct contact with the absorbent material in the lateral direction while constraining in place the super-absorbent oleophilic material. This device may either be used as the only device for removal of such mobile material, used concurrently with a surgical procedure or it may be secondarily utilized following an associated surgical procedure.

An outer envelope of permeable nature may be utilized to contain the super-absorbent microfibers so that the microfibers are held inside the envelope. As the device is utilized, the outer envelope will act to hold the structurally weak microfibers in place, inside the containing sock.

The components of the device are all to be medically sterilizable. The rate of flow of blood through the super-absorbent material must be low enough so that the differential pressure across it does not cause it to be compressed so much as to prevent necessary flow through the device.

The use of oleophilic absorbent material incorporated in this device in combination with surgery is such that the fatty plaque may be moved from the vicinity of the vascular occlusion and elsewhere within the patient vascular system completely. The loosened fatty plaque is absorbed by oleophilic super-absorbent material. The obstruction is therefore permanently removed from the vascular system of the patient.

The combination of both the oleophilic absorbent material and an accompanying surgical procedure makes this device uniquely effective at removal of vascular debris of oleophilic type. Vascular occlusions, vascular blockage, vascular obstructions and vascular debris are all more effectively removed from blood vessels by the combination of incorporated elements of this device and accompanying vascular surgery than with any previously disclosed devices.

Prior art shows the limited ability to move occlusive material from the immediate vicinity of the occlusive blockage. Mostly, this has been done with surgery. The limitation of prior art is in the lack of complete removal of the blockage. Further limitations of prior art are in the true removal of the occlusive fatty material from the entire vascular system.

Specifically, this device may be used during or after an angioplasty procedure. The mobile material moved by angioplasty may subsequently be removed from blood vessels completely by use of the device of this invention. In essence, this device can be used to remove from the vascular system that material which was merely dislocated by angioplasty. All vascular surgery has an inherent risk of creating subsequent occlusions. Loosened fatty material in the vicinity of the surgery is freed to redeposit elsewhere in the circulatory system of the patient. It is this inherent risk that this device seeks to eliminate.

Also, this device may be used after surgical implantation of a vascular stent. The implantation of a vascular stent is useful to increase the inner area of a blood vessel. Unfortunately, the stent may free mobile material from its pre-surgical vascular location. The moved mobile material can become lodged elsewhere in the vascular system so that a secondary vascular occlusion results. If this device is used to cleanse patient blood following the implantation of a surgical stent, the fatty material loosened by that implantation will be removed entirely from the vascular system.

The combination of vascular surgery with use of super-absorbent oleophilic material of this device makes it unique in removing oleophilic vascular occlusions. Surgery alone, or absorbent material alone may not be sufficient to completely remove the offending obstructive fatty debris. Displacement of the oleophilic occlusion via surgery and the subsequent absorption of the loosened obstruction by the super-absorbent material makes this device uniquely useful and superior to devices and procedures in the prior art.

Use of this device may begin by clamping off the offending vascular occlusion, isolating it from the rest of the vascular system. Then, the blood vessel is incised downstream of the offending occlusive location. One catheter is attached to the blood vessel at the incision. The inlet port of the device is connected to the other end of this catheter. This catheter is fixed to the blood vessel downstream of the occlusion. A second catheter is connected to the outlet port of the device and also to the other end of the incised vessel, downstream of the connection point described above. This second catheter and the blood vessel are fixed together also.

The function of this device is the removal of suspended vascular fatty debris from the patient. This is done by forcing patient blood through the device and then back into the patient. Patient blood may be forced through the device by either the patient's own heart or by an external, mechanical, manufactured pump. The device removes the offending suspended, obstructive particles from the patient by directing blood flow out of the patient, absorbing the fatty debris, directing the cleansed blood back into the patient and then disposing of the material cleansed from the patient blood by this device after the patient has been closed.

Generically, the desired oleophilic super-absorbent material is known as meltblown oleophilic microfiber. Oleophilic character is meant to describe a fiber that is of relatively non-polar nature. Conversely, oleophobic character is meant to describe a fiber that is of relatively polar nature. Oleo as a prefix, is known to those practiced in the science as being of an oil-like nature. An oleophilic nature means that an entity is oil-like or fatty. Something that is described as oleophobic, conversely, is of a nature that literally does not like oil or, is the opposite of being fatty. The composition of these oleophilic microfibers may be any polyolefinic polymer, including but not limited to, polyethylene, polypropylene, and polytetrafluoroethylene.

The important characteristics of microfibers used in the super-absorbent material of this device are that they must be strongly oleophilic, be able to absorb and retain fatty plaque debris and also remain sufficiently separated from each other so that open pathways are maintained for free flow of blood. The meltblown oleophilic microfibers must have sufficient bulk strength to remain together as a unit within this device. It is melt-blown by the manufacturer into a fluffy mass of non-woven, microscopic fibers. Fiber orientation is not critical to the functioning of the device. Random fiber orientation is preferred. The fibers are self-bonded by the manufacturer, stretched and ironed somewhat flat. The melt-blown fluffy mass of non-woven, microscopic super-absorbent oleophilic fibers is quite low in bulk density and bulk strength.

Said microfibers are characterized as having an extremely high surface area-to-volume ratio. The microfiber denier and bonding must be balanced so that the fatty absorbent character and bulk strength are maximized while the space between all microfibers is large enough to allow non-oleophilic blood components to pass through unimpeded.

The desired component absorbent material is known by the trade description "Super Absorbent". This material is commercially available. One good example of oleophilic super-absorbent material is Oil Sorbent Type 156. A very similar product is Oil Sorbent Type 159. These products are manufactured by 3M© Company and sold as Type 156 or Type 159 "Oil Sorbent" pads, mats, and sheets.

Although this invention has been described in reference to preferred embodiments, workers skilled in the art will recognize that changes may be made in form and detail without departing from the essence, spirit and scope of the invention. Even though a common vascular surgical procedure such as angioplasty or a common vascular occlusion removal device such as a stent is referred to in this specification, there exist many other procedures and devices in the art with which patients will benefit when used in combination with the utilization of this invention.

SURGICAL PROCEDURE TO USE THIS DEVICE

The surgical procedure involves the following in order:
1) Prepare the patient for invasive surgery.
2) Isolate the subject portion of the occluded vessel.
3) Clamp the vessel to be incised downstream of the vessel occlusion.
4) Make one incisions in the vessel as prepared above.
5) Attach a catheter to the vessel through the above mentioned incision.
6) Connect the other end of the catheter to the inlet port of a blood pump.
7) Connect the outlet port of the blood pump to the inlet port of the device.
8) Fix the incision and the catheter securely.
9) Attach one end of a second catheter to the outlet port of this device and the other end of it to the second of the incised blood vessel.
10) Perform the vascular surgical procedure if desired.
11) Prepare for vascular blood cleansing by surgically removing as much debris as possible.
12) Pass vascular blood from the incised blood vessel into the catheter/pump/device assembly and then back into the patient through the second incised blood vessel end.
13) Pump the patient blood into the inlet port of the device, through the device and back to the patient while monitoring pressure differential across the inlet and outlet ports of the device.
14) Maintain blood flow through the device as desired while assuring that the dynamic pressure differential across the inlet and outlet ports does not exceed a maximum value.
15) After the patient blood has recirculated for sufficient time, stop pumping the blood.
16) Isolate the catheter/pump/device assembly from the patient vascular system.
17) Remove the catheters, pump and device from the blood vessel.
18) Suture the incisions of the blood vessels.
19) Discard the device and its contents.

What is claimed is:

1. A vascular occlusion plaque and fatty blood component removal device comprising:
   (a) oleophilic super-absorbent polymeric microfibers having a diameter less than 10 microns;
   (b) a porous support structure for said oleophilic super-absorbent polymeric microfibers;
   (c) a pump which forces patient blood through the oleophiolic super-absorbent polymeric microfibers and;
   (d) a containment vessel which holds said oleophilic super-absorbent polymeric microfibers and said porous support structure.

2. The device of claim 1 wherein said containment vessel contains said oleophilic super-absorbent polymeric microfibers and wherein said oleophilic super-absorbent polymeric microfibers are at least 500 microns in length and in random orientation.

3. The device of claim 2 wherein said oleophilic super-absorbent polymeric microfibers are contained within a porous support structure of woven material which acts to hold the oleophilic super-absorbent polymeric microfibers in place.

4. The device of claim 2 wherein said pump, porous support structure and oleophilic super-absorbent polymeric microfibers are of sufficiently high molecular weight that they are medically sterilizable.

5. The device of claim 2 wherein said oleophilic super-absorbent polymeric microfibers are self bonded to form a mass.

6. The device of claim 2 wherein the pump may be a patient's own heart.

7. The device of claim 2 wherein the pump may be a mechanical pump.

8. A removal device which removes fatty substances by absorption from vascular blood, comprising:
   (a) oleophilic super-absorbent polymeric microfibers having a fiber diameter less than 10 microns and random fiber orientation;
   (b) a porous support structure for said oleophilic super-absorbent polymeric microfibers;
   (c) a pump which forces patient blood through said oleophilic super-absorbent polymeric microfibers;
   (d) a containment vessel which holds said oleophilic super-absorbent polymeric microfibers;
   (e) an inlet port which conducts vascular blood from a patient to the super absorbent polymeric microfibers; and
   (f) an outlet port.

9. The device or claim 8 wherein said oleophilic super-absorbent polymeric microfibers are contained within a porous support structure of material which acts to hold the oleophilic super-absorbent polymeric microfibers in place.

10. The device of claim 8 capable of removing an amount of fatty lipids equal to at least a mass of the oleophilic super-absorbent microfibers.

11. A device which removes fatty substances by absorption from vascular blood, comprising:

non-porous oleophilic super-absorbent polymeric microfibers having a fiber diameter less than 10 microns;

a porous support structure for said oleophilic super-absorbent polymeric microfibers;

a pump which forces patient blood through said oleophilic super-absorbent polymeric microfibers;

a containment vessel which holds said porous support structure and said oleophilic super-absorbent polymeric microfibers.

12. The device of claim 11 wherein said fiber diameter is less than 5 microns.

13. The device of claim 12 wherein said oleophilic super-absorbent polymeric microfibers are made of a material selected from the materials comprising polyethylene, polypropylene and poly tetrafluomethylene.

14. The device of claim 13 wherein said oleophilic super-absorbent polymeric microfibers are self bonded.

15. The device of claim 14 wherein said oleophilic super-absorbent polymeric microfibers have a random orientation.

* * * * *